United States Patent [19]

Preusser et al.

[11] Patent Number: 4,586,986

[45] Date of Patent: May 6, 1986

[54] METHOD OF RECOVERING PURE AROMATIC SUBSTANCES

[75] Inventors: Gerhard Preusser, Essen; Martin Schulze, Neviges; Gerd Emmrich, Essen; Hans-Christoph Schneider, Hattingen, all of Fed. Rep. of Germany

[73] Assignee: Krupp-Koppers GmbH, Essen, Fed. Rep. of Germany

[21] Appl. No.: 652,161

[22] Filed: Sep. 18, 1984

Related U.S. Application Data

[63] Continuation of Ser. No. 412,860, Aug. 30, 1982, abandoned.

[30] Foreign Application Priority Data

Sep. 5, 1981 [DE] Fed. Rep. of Germany ....... 3135319

[51] Int. Cl.$^4$ ............................................. B01D 3/40
[52] U.S. Cl. ...................................... 203/22; 203/25; 203/27; 203/74; 203/77; 585/808; 585/865
[58] Field of Search ...................................... 203/21–27, 203/58, 74, 77, 81; 585/807, 808, 860, 865

[56] References Cited

U.S. PATENT DOCUMENTS

| | | | |
|---|---|---|---|
| 2,168,570 | 8/1939 | Kraft | 203/27 |
| 2,276,089 | 3/1942 | Ragatz | 203/22 |
| 2,400,370 | 5/1946 | Placek | 203/22 |
| 3,639,497 | 2/1972 | Martel et al. | 203/25 |
| 4,081,355 | 3/1978 | Preusser et al. | 203/58 |
| 4,246,073 | 1/1981 | Umeda et al. | 203/25 |
| 4,256,541 | 3/1981 | Muller et al. | 203/25 |
| 4,278,505 | 7/1981 | Danulat et al. | 203/58 |
| 4,306,942 | 12/1981 | Brush et al. | 203/25 |
| 4,349,416 | 9/1982 | Brandt et al. | 203/21 |

FOREIGN PATENT DOCUMENTS

| | | | |
|---|---|---|---|
| 347828 | 1/1922 | Fed. Rep. of Germany | 203/22 |
| 16414 | 2/1979 | Japan | 203/27 |

*Primary Examiner*—Wilbur Bascomb
*Attorney, Agent, or Firm*—Michael J. Striker

[57] ABSTRACT

Disclosed is a method for recovering pure aromatic substances from a mixture of hydrocarbons containing both aromatic and non-aromatic fractions. The input mixture is fed through an extractive stage provided with a preliminary distillation column. In the preliminary stage the aromatics-containing product is treated at a pressure up to 20 bar and a temperature up to 300° C. The pressure is adjusted to a value at which the operational temperature of the preliminary stage is higher than the pressure and temperature in the extractive stage and the heat of the vapors discharged from the preliminary stage is used for heating the extractive stage.

9 Claims, 2 Drawing Figures

METHOD OF RECOVERING PURE AROMATIC SUBSTANCES

This application is a continuation of application Ser. No. 412,860, filed Aug. 30, 1982, now abandoned.

BACKGROUND OF THE INVENTION

The present invention relates in general to a method of recovering pure aromatic substances of a mixture of hydrocarbons which contains both aromatic and an arbitrary amount of non-aromatic substances. In particular, this invention relates to a method of regaining such aromatics by extractive distillation using N-substituted morpholines as selective solvent, the extraction stage being provided with a preliminary after-treatment distilling means.

For separating aromatic substances from mixtures of hydrocarbons by means of extractive distillation with N-substituted morpholines with or without addition of water to serve as selective solvents, is known from prior art. For example, in German Pat. Nos. 1,568,940 and 2,040,025, two methods of this kind have been described which have found large-scale application in practice. It is also conventional, particularly when an extractive distillation stage is used, to subject the charged product, namely the mixture of hydrocarbons, to a preliminary distillation before it is applied to the extraction stage. Normally, the extraction stage consists of one or more extraction columns connected to an output column in which the solvent is separated from the extracted product containing the aromatic substances by distillation. The preliminary distillation serves for separating undesired substances from the charged product before its feeding in the extraction stage. In the case when the charged-in product contains a plurality of aromatics, such as for example benzene, toluene and xylene, the extracted product freed from solving agent must undergo in the additional distillation means (after-treatment distillation) a treatment for decomposing the extract from the aforementioned fractions.

In spite of the fact that the methods described in the aforementioned patent literature have found broad application for recovering aromatics, attempts are still being made to improve such prior-art methods, particularly to reduce the consumption of energy in said methods.

SUMMARY OF THE INVENTION

A general object of the present invention is the improvement of known methods of this kind.

In particular, it is an object of the invention to provide a method of recovering aromatics by means of which a distinct energy saving is achieved.

In keeping with this object and others which will become apparent hereafter, one feature of the invention resides, in the steps of exposing the mixture in the preliminary distillation means to a pressure up to 20 bar and a temperature up to 300° C., adjusting the pressure to a value at which the operational temperature of the preliminary distillation means is higher than that of the extractive stage, and using the heat content of vapors from the preliminary distillation means for heating the extractive stage.

The method of this invention thus provides a heat exchange between the extraction stage and the preliminary distillation stage, in such a manner that the latter stage is operated at an increased pressure and at such a temperature which makes it possible to employ the heat content of the produced vapors for heating the columns in the extraction stage. In comparison to a preliminary distillation operating at normal pressure, it is possible to achieve an energy reduction during the entire process which may exceed 40%.

In view of the fact that the components of the hydrocarbon mixture used as the starting product for the recovery of aromatics are usually complicated multi-fraction compounds, in operating the method according to this invention the fact must be taken into account that, in contrast to operation at normal pressure, the distillation of such multi-component mixtures at increased pressure brings about the shifting of distillation conditions (azeotropic formation, boiling point, and the like) in such a manner which cannot be predicted by theoretical computation. The same conditions are of course also valid then when increased pressure is employed also in the after-treatment distillation stage and the multi-fraction mixture is for example composed of benzene, toluene and xylene. It should also be taken into consideration that, in using distillation under increased pressure, higher operational costs and installation costs will result, in comparison to distillation at normal pressure. Such increased costs are caused for example by substantially higher return flow, by increased number of buffers in the columns, as well as by the more expensive construction of the columns. In considering all these circumstances, it would at first sight seem not worthwhile, for the purpose of saving energy, to substitute the preliminary distillation operating at normal pressure by that designed for high-pressure operation. The substantial energy saving achieved by the method of this invention therefore is completely surprising.

The method of this invention is preferably performed so that the preliminary distillation column is operating at higher pressure, whereby the heat of output vapors is employed for heating the columns in the extraction stage, which is operated at normal pressure or under a moderately increased pressure up to 3 bar. In the extraction stage there is used normally a one- or multiple-stage extractive distillation. It is also possible to use a liquid-liquid extraction or the combination of liquid-liquid extraction and extractive distillation. In another modification of the method of this invention, there is provided an additional distillation connected to the outlet side of the extraction stage (the so-called after-treatment distillation), which serves for a further separation of the recovered extract into respective fractions of the aromatic substances, and is operated under increased pressure, whereby the produced vapors are employed for heating the columns in the extraction stage, the latter again operating under normal pressure or moderately increased pressure up to a maximum of 3 bar.

Vapors produced in the preliminary distillation can also be used for preheating in an indirect heat exchange the charging product.

The return flow ratio to be maintained in the preliminary distillation is, as a rule determined not only by the separating task to be handled. This return flow ratio and the number of buffers or bottom plates in the preliminary distillation columns are selected such that the amount of vapors produced at the top of the columns is sufficient for heating the columns in the extraction stage, as well as, if desired, for the preliminary heating of the feed.

The feed or charge-in product suitable for the method of this invention is preferably pressure-refined product of coking benzene, hydrogenized pyrolysis benzene, reformated benzene, as well as other benzene-, toluene- and xylene-containing mixtures of hydrocarbon substances.

When the preliminary distillation is carried out under increased pressure, the produced vapors in some circumstances may contain an increased amount of certain non-aromatic substances such as methylcydohexane for example. Inasmuch as such vapors after their condensation are used as the charging product for the subsequent extraction stage, there may occur problems because these non-aromatic substances when certain solving agents are used in the extraction stage, are separable from the aromatics only with great difficulty. These problems are avoided in the method according to this invention because there are employed N-substituted morpholines as selective solvent. In particular, the N-formyl morpholine has proved to be a particularly suitable solvent. Such solving agents can be employed with or without the addition of water. If water is added to the solvent, in the case of liquid-liquid extraction, the water content is normally 15% by weight, and between 0 and 8% by weight in the case of extractive distillation.

The novel features which are considered characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DESCRIPTION OF THE PREFERRED EMBODIMENTS

The illustrated flow diagrams depict schematically only those devices which are unconditionally necessary for an explanation of the method of this invention, whereas the other auxiliary devices, such as valves and pumps, are omitted for the sake of clarity.

Figure 1:
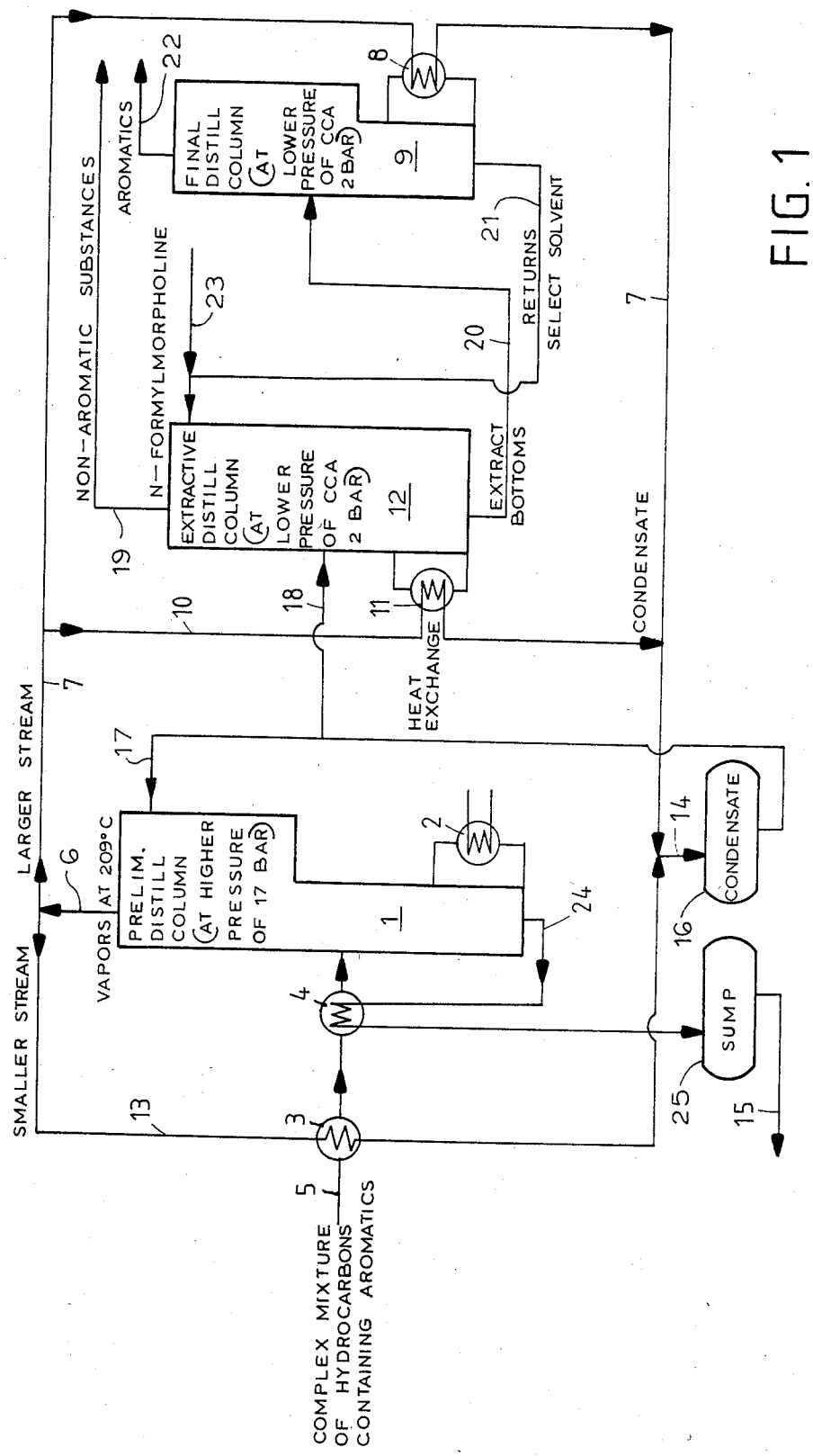
FIG. 1 is a flow diagram of one embodiment of the process according to this invention, using a preliminary distillation under increased pressure and an extractive distillation.

In the process according to FIG. 1, a preliminary distillation column 1 is operated under increased pressure. The charge-in product or feed constituted by a mixture of hydrocarbons containing aromatic substances, is fed through conduit 5 through indirect heat exchangers 3 and 4 in the center of the preliminary distillation column 1, which is provided with a plurality of buffers or bottom plates. At the bottom end portion of the column 1 there is provided a heater 2 for recirculating sump or residue. The pipe system of heater 2 can be heated by high-pressure steam or by a non-illustrated oven. The outlet vapors discharged from the top end portion of the preliminary distillation column 1 are withdrawn through conduit 6. In this example, the stream of vapors in conduits 6 is divided into two partial streams. A larger partial stream flows through conduit 7 in the pipe system of a heater 8 for recirculating sump in the output or after-treatment distillation column 9, so that heat from this larger stream is used for heating the latter output column 9. At the same time, a branch conduit 10 supplies a part of the larger stream in conduit 7 to another heater for recirculating sump in extractive distillation column 12 to serve for heating the latter.

A smaller partial stream from conduit 6 at the top of column 1 is supplied via conduit 13 in the pipe system of the indirect heat exchanger 3, in which the heat content of vapors is used for preheating the feed from conduit 5. As will be seen from the flow diagram, condensates produced at the outlet of heat exchanger 3 and at the outlets of heaters 8 and 11 are delivered through collecting conduit 14 into a condensate-collecting vessel 16 where the condensed top product from the preliminary distillation column 1 is accumulated. A smaller partial stream of this condensed top product in vessel 16 is recirculated through conduit 17 into the top part of column 1, whereas the major part of the condensate from vessel 6 is delivered through conduit 18 as a feed in the central portion of the extractive distillation column 12. Column 12 is also provided with buffers or bottom plates.

The extraction stage, i.e. the extractive distillation column 12, and the assigned output column 9 operate at a pressure which is substantially below the operational pressure of the preliminary distillation column 1. Otherwise, the extraction stage operates according to conventional principles of the extractive distillation. In other words, non-aromatic substances are discharged from the top end part of extractive distillation column 12 via conduit 19, whereas the extract which contains the aromatic substances and the solvent is removed from the sump of column 12 through conduit 20 and introduced in the central part of output column 9. In the latter column, the aromatics are distillatively separated from the selective solvent. The selective solvent is removed through conduit 21 from the sump of the output column 9 and returned to the top part of the extractive distillation column 12, whereas the simultaneously retrieved aromatics are discharged through conduit 22 from the top part of the output column 9. If desired, fresh dissolving agent is fed through conduit 23 into the circuit for the solvent.

The sump product from the preliminary distillation column 1 is withdrawn through conduit 24 and supplied via the heat exchanger 4 in a collecting vessel 25, from which it is discharged through conduit 15. The heat content of the sump product is transferred in the indirect heat exchanger 4 to the starting mixture fed through conduit 5.

Figure 2:
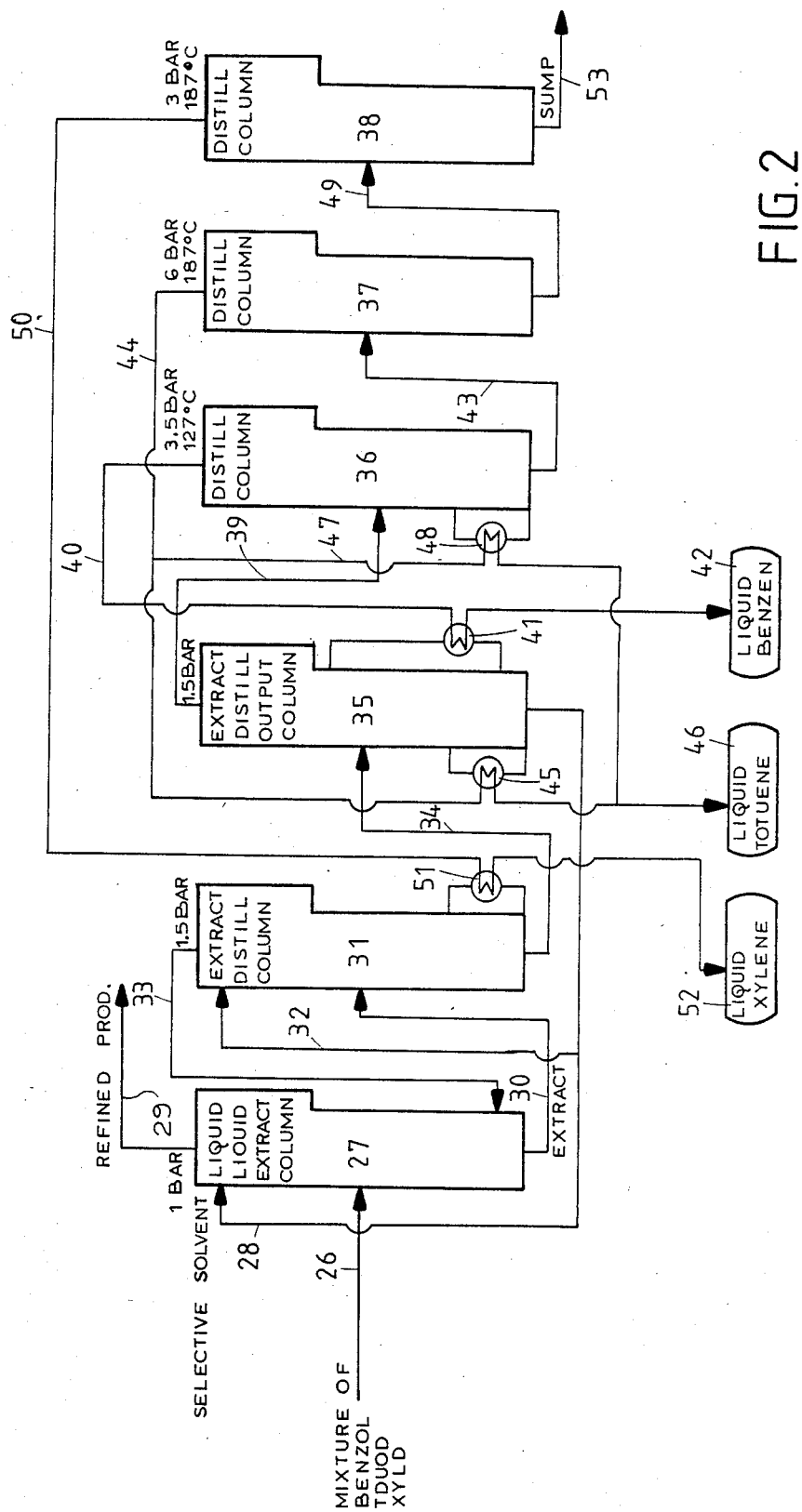
FIG. 2 is a flow diagram of another embodiment of this invention, using an extraction stage which is a combination of liquid-liquid extraction and extractive distillation and employing an after-treatment or outlet distillation under increased pressure.

The modification of the method of this invention illustrated in the flow diagram of FIG. 2 is employed particularly in the case when a multi-fraction starting product is used from which, apart from the benzene fraction, also the toluene and xylene fractions are to be recovered. The starting product in this example is fed through conduit 26 in the central part of a liquid-liquid extractor 27, which is provided with buffers or bottom plates. Solvent is fed through conduit 28 into the top end part of the liquid-liquid extractor 27. Refined product is discharged from the top part of column 27 through conduit 29 whereas the produced extract is fed through conduit 30 in the central part of the subsequent extractive distillation column 31. This column 31 is also provided with buffers or bottom plates and supplied through conduit 32 with the required solvent. The addition of the solvent in column 31 is also effected in the top end part of the column. The top product from the extractive distillation column 31 is fed through conduit 33 and applied as the so-called countersolvent in the bottom end part of the liquid-liquid extractor 27. The extract accumulated in the sump of the column 31 is applied through conduit 34 in the central part of the output column 35, in which the aromatic substances contained in the extract are separated by distillation from the solvent. The solvent is accumulated in the sump of the output column 35 and is recirculated through conduits 28 and 32 into the columns 27 and 31. The top end product discharged from the output column 35 contains the fractions of aromatic substances and therefore has to be subjected to a further fractionation.

For this purpose there is provided a series of cascade-connected distillation columns 36, 37, 38 which according to this invention are operated under higher pressure and at a higher temperature than the columns of the extraction stage, namely of the liquid-liquid extractor 27, the extractive distilation column 31, and the output column 35. The product discharged from the end portion of the output column 35 is fed firstly through conduit 39 in the central part of the distillation column 36, designed for separating benzene fraction. Accordingly, the distillation column 36 similarly as the subsequent distillation columns 37 and 38 is equipped with installations such as bottom plates or filling bodies, and the like, which are well known in conventional distillation techniques. The benzene fraction, as mentioned above, is withdrawn from the top of the distillation column 36. The benzene vapors are fed through conduit 40 to a heat exchanger 41 pertaining to the output column 35 of the extraction stage. In the heat exchanger 41 the stream of water-containing products from the column 35 is heated in the indirect heat exchanger by the benzene vapors, so as to produce the so-called strip steam. In doing so, the benzene vapors become condensed, so that benzene reaches the collecting vessel 42 in liquid state and is discharged therefrom for further utilization.

The sump product from the distillation column 36 in the meantime is fed through conduit 43 in the distillation column 37, which serves for separating toluene fraction. Toluene vapors discharged from the top end portion of column 36 are fed through conduit 44 through heater 45 for recirculating sump in the output column 35. In the heater 45 a condensation of the vaporous toluene product takes place, so that toluene in liquid phase reaches the collecting container 46. A bypass conduit 47 can be provided for leading a part of the toluene vapors from the conduit 44 to heater 48 for recirculating sump in the distillation column 36. The bypass conduit 47 is connected to the downstream part of the conduit 44 before its connection to collecting vessel 46.

The sump product from the distillation column 37 is fed again through conduit 49 into the central part of the final distillation column 38, which serves for separating xylene. The xylene-containing vapors are again discharged through the top end part of the column 38 and are fed through conduit 50 into the heater 51 for recirculating sump in the extractive distillation column 31. In the heater 45, similarly as in the corresponding heaters of the aforedescribed columns, the xylene-containing vapors are condensed and xylene reaches in liquid condition the assigned collecting vessel 52, wherefrom it is discharged for further processing (separation). The sump product of the final distillation column 38 is withdrawn through conduit 53 and still contains traces of $C_9$-aromatics.

In the following examples, the effectiveness of the method of this invention is disclosed:

EXAMPLE 1

This example relates to recovery of pure benzene from a pressure-refined coke benzene, the initial or starting product being treated according to the flow diagram of FIG. 1, namely it is subjected first to a preliminary distillation and the resulting top end product is fed in an extractive distillation column operating with N-formylmorpholine as selective solvent.

The starting product in this example has the following composition:

| | |
|---|---|
| $C_5$ — hydrocarbon | 0.04 weight-% |
| $C_6$ — hydrocarbon | 0.78 weight-% |
| methylcyclopentane | 0.20 weight-% |
| iso $C_7$ — hydrocarbon | 0.12 weight-% |
| cyclohexane | 0.35 weight-% |
| $nC_7$ + dimethylcyclopentane | 0.16 weight-% |
| methylcyclohexane | 0.25 weight-% |
| benzene | 75.30 weight-% |
| paraffinic $C_8$ — hydrocarbon | 0.07 weight-% |
| dimethylcyclohexane | 0.48 weight-% |
| toluene | 20.05 weight-% |
| $C_8$ — aromatics | 2.20 weight-% |

In the first embodiment of the example, operation proceeds in accordance with conventional prior-art techniques. That is, the feed is subject in the preliminary distillation stage to normal pressure (pressure at the top end of the column is a maximum of 1.1 bar), whereby the product discharged from the top part in the preliminary column is fed in the subsequent extractive distillation column operating at a pressure of 2 bar. A heat exchange between the preliminary distillation and the extractive stage in this instance does not take place. The product recovered at the top end part of the output column, in this example pure benzene, contains 100 ppm toluene and 350 ppm non-aromatic impurities. The recovery of benzene amounts to 99.8%. The total heat consumption of the method is as follows:

| | |
|---|---|
| preliminary distillation column | 1,440 kJ/kg benzene |
| extraction stage | 920 kJ/kg benzene |
| = total heat consumption | 2,360 kJ/kg benzene |

In the second embodiment of the example, in contrast to the first embodiment, the preliminary distillation of the same starting product is made under the following conditions in accordance with this invention:

| | |
|---|---|
| pressure at the top part of the column | 17 bar |
| temperature at the top part | 209° C. |
| sump temperature | 281° C. |
| return flow ratio | 1:3.2 |

The operating condition in the extraction stage (extractive distillation+output distillation) in comparison to the first embodiment, was only negligibly changed, that is due to higher contents of methylcyclohexane in the product from the top part of the preliminary distillation column, the proportion of the solvent used in the extractive distillation has been slightly increased. Purity and yield of the produced benzene waas practically the same as the purity and yield in the first part of the example. According to the method of this invention, however, vapors from the top part of the preliminary distillation column have been employed for heating the columns in the extractive stage, resulting in the following heat consumption:

| preliminary distillation | 1,270 kJ/kg benzene |
|---|---|
| extraction stage | 1,230 kJ/kg benzene |

In comparison to the preliminary distillation under normal pressure (first embodiment) the heat consumption in the preliminary distillation under increased pressure (second embodiment), in spite of slightly higher return flow ratio, is lower because, due to the high working pressure, the vaporization heat is about 30% lower. In the method according to this invention, moreover, it is no longer necessary to supply heat energy to the extraction stage in form of separate energy, for example steam. The heat requirements are now completely covered by the heat content of vapors produced at the top part of the preliminary distillation. The temperature of the top part product of 209° C. is thus fully sufficient. In practice, there is required only 80–90% of the amount of the top vapors for heating the extraction stage, so that the remainder of the heat energy can be utilized for preliminary heating of the initial feed. The total heat requirement for the second embodiment of the example is therefore covered only with 1,270 kJ/kg benzene.

By comparison of the results of the first part of the example with the second part thereof, it will be seen that, for the second embodiment, only $$\frac{1,270 \cdot 100}{2,360} = 54\%$$

of the heat consumption in part is necessary. The achieved energy saving amounts therefore to 46%.

EXAMPLE 2

This example is concerned with the recovery of pure benzene from a fully hydrated pyrolysis benzine. The starting product or feed has the following composition:

| $C_5$ — hydrocarbon | 0.06 weight-% |
|---|---|
| $C_6$ — hydrocarbon | 1.23 weight-% |
| methylcyclopentane | 4.73 weight-% |
| iso $C_7$ — hydrocarbon | 1.97 weight-% |
| cyclohexane | 2.05 weight-% |
| n $C_7$ + dimethylcyclopentane | 2.59 weight-% |
| methylcyclohexane | 1.05 weight-% |
| benzene | 60.20 weight-% |
| paraffinic C 8 - hydrocarbon | 0.99 weight-% |
| dimethylcyclohexane | 0.96 weight-% |
| toluene | 23.97 weight-% |
| $C_8$ — aromatics | 0.20 weight-% |

The first and second embodiment of the experiment correspond in principle to those disclosed in Example 1.

For the first embodiment of the experiment (preliminary distillation under normal pressure) the following heat requirements result:

| preliminary distillation | 1,290 kJ/kg benzene |
|---|---|
| extraction stage | 1,000 kJ/kg benzene |
| = total heat requirement | 2,290 kJ/kg benzene |

The recovered pure benzene contains still 100 ppm toluene and 400 ppm non-aromatics as impurities.

In the second embodiment of the experiment, the preliminary distillation is made under the following conditions:

| pressure at the top of the preliminary column | 17 bar |
|---|---|
| temperature at the top part | 209° C. |
| sump temperature | 252° C. |
| return flow ratio | 1:3.6 |

For the heat requirements the following values result:

| preliminary distillation | 1,420 kJ/kg benzene |
|---|---|
| extraction stage | 1,290 kJ/kg benzene |

Inasmuch as, even in this example, the heat requirements for the extraction stage are completely covered by the heat content of the vapors from the top part of the preliminary distillation column, the following computation is valid for the heat requirements of the second embodiment, relative to the first embodiment, of the experiment:

$$\frac{1,420 \cdot 100}{2,290} = 62\%$$

The resulting energy saving amounts to 38%.

EXAMPLE 3

Whereas Examples 1 and 2 refer to the flow diagram of FIG. 1, the present example is employed for the preparation of the so-called reformed benzine or gasoline, for which the flow diagram according to FIG. 2 is employed. The starting product in this example has the following composition:

| benzene | 7 weight-% |
|---|---|
| toluene | 26 weight-% |
| $C_8$ — aromatics (xylenes) | 28 weight-% |
| non-aromatics | 39 weight-% |
| $C_9$ — aromatics | traces |

In the extraction stage, consisting of a liquid-liquid extractor, extractive distillation column, as well as an output distillation column, the free aromatic mixture is first recovered under the use of N-formylmorpholine as selective solvent. Subsequently, this aromatic mixture in the cascade-connected after-treatment distillation columns, is fractioned into its components. The detailed process steps have been disclosed previously in connection with FIG. 2. The liquid-liquid extractor 27 is operated at a pressure of 1 bar, the extractive distillation column 31 at a pressure of 1.5 bar, and the output distillation column 35 at a pressure of 1.5 bar. In this case, it is again N-formylmorpholine which is employed as selective solvent.

In the first embodiment of the experiment, which is again performed according to conventional techniques, the after-treatment distillation takes place in the distillation columns 36, 37, 38 under normal pressure, or at a slightly increased pressure, whereby both for the extraction stage and for the after-treatment distillation a separate heating of each column is necessary. For the heat consumption requirement, the following computation applies:

|   |   |
|---|---|
| extraction stage | 1,821 kJ/kg aromatics |
| after-treatment distillation | 1,332 kJ/kg aromatics |
| = total heat requirement | 3,153 kJ/kg aromatics |

In the second embodiment of the experiment, the after-treatment distillation has been made under increased pressure, whereby the following conditions have been obtained in respective distillation columns:

|  | Distillation column: | | |
|---|---|---|---|
|  | 36 | 37 | 38 |
| Pressure at top of column | 3.5 | 6 | 3 |
| Top temperature (°C.) | 127 | 187 | 187 |
| Return flow ratio | 1:2.5 | 1:7 | 1:8 |

Vapors discharged from top parts of respective distillation columns 36, 37, 38 are employed, according to the method of FIG. 2, for heating columns in the extraction stage and completely cover the heat requirements of the latter. In the method of this invention, therefore, the heat requirement of the after-treatment distillation is to be considered. This heat requirement is met at 2,160 kJ/kg aromatics. Under the same yield and the same purity of the produced aromatics, the following heat requirement for the second embodiment, with respect to the first part, of the experiment the following computation applies:

$$\frac{1,160 \cdot 100}{3,153} = 68.5\%$$

The energy saving amounts thus to 31.5%.

The above examples prove the effectiveness of the method of this invention and show that at equal purity and yield the recovery of the aromatic fractions can be effected at substantial energy savings.

It will be understood that each of the elements described above, or two or more together, may also find a useful application in other types of constructions differing from the types described above.

While the invention has been illustrated and described as embodied in specific examples of the recovery of aromatic fractions, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of recovering high-purity aromatic fractions from a complex mixture of hydrocarbons containing aromatic and non-aromatic constitutents, comprising the steps of feeding the mixture in a preliminary distillation stage and distilling the mixture at an operational pressure in a range up to 20 bar and an operational temperature in a range up to 300° C.; discharging vapors from the top of the preliminary distillation stage; using the heat content of at least a part of the discharged vapors for heating an extractive distillation stage and simultaneously condensing said vapors; extractivelly distilling the resulting condensate in the extractive distillation stage with N-substituted morpholine as selective solvent while adjusting the operational pressure in the preliminary distillation stage to a value at which the operational temperature of the preliminary distillation stage is higher than the temperature of the extractive distillation stage; then separately discharging from the extractive distillation stage the non-aromatic overhead constituents and extract bottoms which contain the aromatic constituents and the selective solvent; and then separating the aromatic constituents from the selective solvent.

2. A method as defined in claim 1, wherein a minor part of vapors discharged from the preliminary distillation stage is used for preliminary heating of said mixture of hydrocarbons before the feeding in the preliminary distillation stage, while a major part of said vapors is used for heating said extractive distillation stage.

3. A method as defined in claim 2, wherein the preliminary distillation stage includes a column and the major part of vapors produced at the top of the column is sufficient for heating the extractive distillation stage.

4. A method as defined in claim 3, wherein the minor part of vapors produced at the top of the column is sufficient for preliminary heating of said mixture of hydrocarbons.

5. A method as defined in claim 1, wherein said vapors discharged from the preliminary distillation stage are condensed in heat exchanging means used for heating said extractive distillation stage.

6. A method of recovering high purity aromatic fractions from a complex mixture of hydrocarbons containing aromatic and non-aromatic constituents, comprising the steps of distilling the mixture in a preliminary distillation stage, feeding vapors discharged from the top of the preliminary distillation stage into an extractive distillation stage operating with a selective solvent, increasing operational pressure in said preliminary distillation stage relative to that in the extractive distillation stage to obtain a heat content of the discharged vapors which is greater than heat required for heating the extractive distillation stage, using the heat content of at least a part of the discharged vapors for heating the extractive distillation stage, separately discharging from the extractive distillation stage the non-aromatic overhead constituents and extract bottoms which contain the aromatic constituents and the selective solvent, and separating the aromatic constituents from the selective solvent.

7. A method as defined in claim 6, wherein in extractive distillation stage is operated under pressure between 1 and 3 bar.

8. A method as defined in claim 6, wherein N-formylmorpholine is employed as selective solvent for the extractive distillation stage.

9. A method as defined in claim 6 wherein a minor part of the discharged vapors is used for heating the mixture of hydrocarbons before its feeding in the preliminary distillation stage while a major part of vapors is used for heating the extractive distillation stage.

* * * * *